United States Patent [19]

Pasternack

[11] 4,180,235

[45] Dec. 25, 1979

[54] THROTTLING DEVICE FOR FLUIDS

[75] Inventor: Adalbert Pasternack, Bad Schwartau, Fed. Rep. of Germany

[73] Assignee: Drägerwerk Aktiengesellschaft, Fed. Rep. of Germany

[21] Appl. No.: 866,237

[22] Filed: Jan. 3, 1978

[30] Foreign Application Priority Data

Jan. 7, 1977 [DE] Fed. Rep. of Germany ....... 2700491

[51] Int. Cl.² .............................................. F16K 7/06
[52] U.S. Cl. ......................................... 251/8; 138/45; 138/46; 251/205
[58] Field of Search ..................................... 251/4–10, 251/205; 138/45, 46

[56] References Cited

U.S. PATENT DOCUMENTS

| 2,827,919 | 3/1958 | Rice et al. | 137/505.47 |
| 3,584,830 | 6/1971 | Koehn | 251/8 |

FOREIGN PATENT DOCUMENTS 643812  9/1950  United Kingdom ................... 24/135 R Primary Examiner—Martin P. Schwadron
Assistant Examiner—Richard Gerard
Attorney, Agent, or Firm—McGlew and Tuttle

[57] ABSTRACT

A throttling device for fluids comprises a flexible tube in which the fluid is conveyed which has a compressible wall to vary the flow cross-section therethrough. The tube is received on a base plate which has a continuous channel of a size to receive the tube, and it is covered by a cover plate which has a projecting surface of a dimension and location to be positionable into the groove for compressing the tube therein, and which further includes control means for moving and the base plate relatively so as to vary the pressure acting on the tube and thus the flow cross-section therethrough.

5 Claims, 3 Drawing Figures

THROTTLING DEVICE FOR FLUIDS

BACKGROUND OF THE INVENTION

1. Field of the Invention

This invention relates in general to the construction of fluid handling devices and in particular to a new and useful device for throttling fluids which flow through a flexible conduit, and which includes a plate member having a groove thereon in which the conduit is positioned and a cover plate which has a projection thereon of a depth to engage in the groove and means for moving the cover plate and base plate relatively in order to press or release the tube and thus regulate the flow cross section therethrough.

2. Description of the Prior Art

In throttling devices, the pressure reduction is generally obtained through narrow gaps. At the same time, it is usual to reduce the pressure along very short distances, whereby high shearing stresses are produced. To fluids sensitive to shear, for example, blood, milk, and albuminous solutions, high shear stresses leading to shearing within the structural constitution are not beneficial. They reduce the quality.

A flow regulator for adjusting desired flow rates of fluids conveyed through lines is known, in which a flexible tube is surrounded by a controllable throttling device which acts on the circumference of the tube and by which the cross-section of passage is varied. The throttling device comprises a fixed abutment and a lever arm mounted for pivoting about its central portion. Upon pivoting one end of the lever arm, the other end presses the tube against the abutment. By the deformation of the tube the cross section of the passage is varied. The movement of the lever arm is controlled by a step motor through a cam plate. In this flow regulator, the variation of the cross-section is limited to a short length of the tube, so that the pressure is reduced over a short distance. This causes high shearing forces in the fluid to be controlled. Therefore, this flow regulator is not suitable for fluids sensitive to shear (German Offenlegunsschrift No. 21 05 106).

Further known is a micro control device for liquids flowing through flexible conduits, in which the rate of flow is controlled by squeezing the conduit walls in one direction, from opposite sides. The wall of the conduit is squeezed by a lever by which the flexible conduit is pressed through an aperture provided in the wall of the device. The lever may be actuated manually or automatically. The flexible conduit is not only squeezed in its cross section, but also deformed along its longitudinal axis. In this micro control device, the pressure is reduced along a short way. That is why the device is not suitable for liquids sensitive to shear. In addition, it is not advantageous that the material of the conduit is subjected to high stresses (German Offenlegunsschrift No. 23 53 624).

SUMMARY OF THE INVENTION

The present invention is directed to a throttling device which produces only small shearing stresses on the handled fluid and thus may be also for fluids sensitive to shear. At the same time, the device is to be usable for medical purposes with high requirements on sterility.

For this purpose, in accordance with the invention, the flexible tube is accommodated in a channel of a base plate into which channel pressure surfaces or lands of a cover plate which are movable against the cross section of the tube, engage.

The advantage obtained with this solution is a simple and reliable operation of the throttling device. The shearing stress $\tau$ at the wall of the flexible tube and the pressure drop $\Delta p$ in the fluid flow are related as follows:

$$\tau = \Delta p \cdot (R/2L)$$

where
R = radius of the tube
L = length of the tube

With a constant inside diameter 2R of the tube and a constant pressure drop $\Delta p$, the shearing stress is inversely proportional to the length L of the tube.

In consequence, if a long tube is used as the conduit for the fluid, a small shearing stress is obtained. This makes the use of the inventive throttling device advantageous also for fluids which are sensitive to shear. The free cross section of the flexible tube accommodated in the channel in accordance with the invention is controlled along the whole length of the tube and the shearing stress is varied correspondingly. The use of a flexible tube makes possible a simple construction with a small number of component parts. The tube can be removed without disassembly costs and may then be sterilized.

According to a development of the invention, the channel is spiral-shaped with connections in the form of tangential portions which extend up to the outer edge of the base plate. The tangential portion leading to the center of the spiral extends below the spiral, is covered by a cover strip, and connects to the spiral through curved portions. The spiral configuration of the channel with tangential connections makes it possible to provide small dimensions of the device even with great tube lengths, whereby the incorporation of the throttling device into the system of conduits is facilitated. The inventive possibility of using great tube lengths permits an accurate and secure metering of the fluid.

Such an accurate and secure metering is made possible by a design in which the cover plate is guided on a central bolt and pressed against the tube by means of a control member which is adjustable in height.

Further advantages result from designing the control member as a lever nut fitting the central bolt which is provided with a thread, or from connecting the control member to an automatic setting device. Thus, in accordance with the desired design, the throttling device may be controlled manually, or automatically through an adjusting mechanism.

In all these embodiments the construction is simple and not only ensures a reliable control and is usable in systems conveying fluids sensitive to shear, but also makes it possible to remove the flexible tube without problems, for purposes of sterilization or disinfection.

Accordingly, it is an object of the invention to provide a throttling device for fluids, which comprises a flexible tube in which the fluid is conveyed which has a compressible wall to vary the flow cross section therethrough and including a base plate having a continuous channel in which the tube is positionable and which is covered by a projection of a cover plate placeable over the base plate and which also includes means for varying the spacing between the cover and the base plate so as to vary the amount that the projection engages the tube and compresses it whereby to vary the flow cross section therethrough.

A further object of the invention is to provide a throttling device for fluid which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 1:
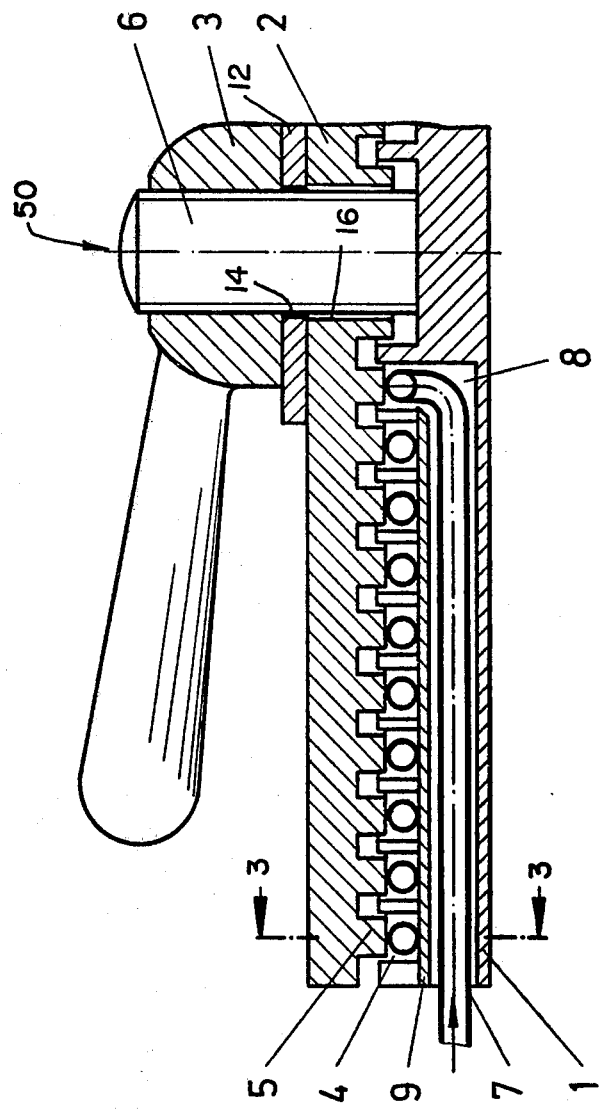
FIG. 1 is a sectional view of a throttling device constructed in accordance with the invention.
Figure 2:
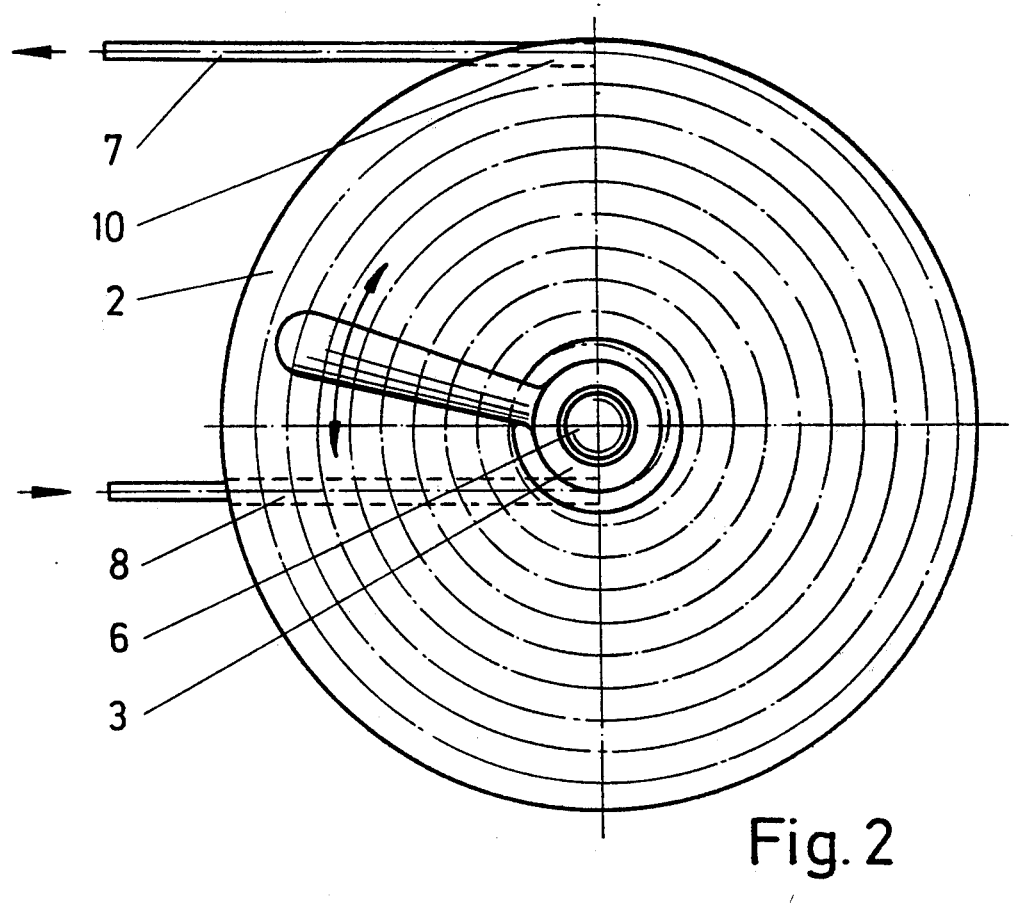
FIG. 2 is a top plan view of the device shown in FIG. 1.
Figure 3:
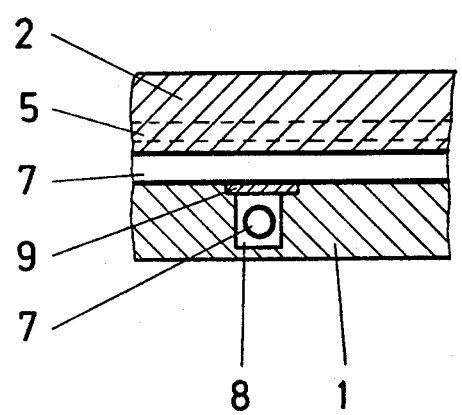
FIG. 3 is a partial sectional view taken along the line 3—3 of FIG. 1.

Referring to the drawings in particular, the invention embodied therein comprises a throttling device generally designated 50 which includes means for varying the flow cross section through a flexible tube or a tube having a compressible wall 7.

The throttling device for fluids to be used in systems with substances which are sensitive to shear, comprises a base plate 1, a cover plate 2 and a control member 3 which latter, in the present example, is designed as a lever nut. Cover plate 2 is movable relative to base plate 1 and, for this purpose, freely guided on a central threaded bolt 6 which is threadably engaged with the lever nut 3. Base plate 1 is provided with a channel 4, and spiral pressure land 5 of cover plate 2 projects into this channel. Both the channel 4 and the pressure land 5 extend spirally about the central axis and due to the guidance of cover plate 2 on central bolt 6, they can reliably be brought into engagement so as to movably fit each other.

A flexible tube 7 conveying the fluid to be throttled is passed through a tangential portion 8 of the spiral channel 4, which portion extends up to the center of the spiral of the channel 4, then through the spiral and through an outer tangential portion 10. Thus, the two tangential portions 8 and 10 of the channel in base plate 1 serve as connections to the outside. To prevent a squeezing of tube 7 in tangential portion 8, this portion is covered by a cover strip 9. For throttling the fluid, i.e. reducing the pressure, the height of the gap between the bottom of channel 4 and pressure land 5 is reduced by turning control member 3, whereby tube 7 is squeezed and its cross sectional area is reduced. The possibility of continuously varying the height of the gap ensures a controlled reduction of the pressure and, thereby, an accurate metering of the fluid. Tube 7 may be exchanged upon removing control member 3 and cover plate 2 and an intermediate plate 12 which has bores 14 and 16, respectively, which are greater than the outside diameter of the threaded bolt 6.

While specific embodiments of the invention have been shown and described in detail to illustrate the application of the principles of the invention, it will be understood that the invention may be embodied otherwise without departing from such principles.

What is claimed is:

1. A throttling device for fluids, comprising a flexible tube in which the fluid is conveyed, having a compressible wall to vary the cross section thereof, a base plate having a continuous spiral channel in which said tube is accommodated, a cover plate overlying said base plate and having a projecting surface of a complementary spiral of a dimension and location such that it projects into said channel to engage and compress said tube therein, and control means for displacing said cover and said base plate relatively for selectively advancing and retracting the projecting surface and groove relatively for varying the flow cross section of said tube.

2. A throttling device for fluids, comprising a flexible tube in which the fluid is conveyed, having a compressible wall to vary the cross section thereof, a base plate having a continuous channel in which said tube is accommodated, a cover plate overlying said base plate and having a projecting surface of a dimension and location such that it projects into said channel to engage and compress said tube therein, and control means for displacing said cover and said base plate relatively for selectively advancing and retracting the projecting surface and groove relatively for varying the flow cross section of said tube, said continuous channel comprising a spiral, said projection comprising a complementary projecting spiral, a tangential channel portion extending tangentially inwardly from the periphery of said base plate to the center of said spiral and a cover strip covering said tangentially extending channel.

3. A throttling device according to claim 2 including a bolt mounted on said base plate, said cover having a bore being engaged over said base plate with the bolt through said bore and a control member displaceable on said bolt for varying the position of said cover relative to said base plate.

4. A throttling device according to claim 3 wherein said bolt has a threaded portion, said control member comprising a nut threaded to said bolt being displaceable thereon toward and away from said cover.

5. A throttling device according to claim 2 wherein said control means comprises a bolt and a nut member threaded on said bolt and engageable with said cover member to urge it toward said base plate.

* * * * *